United States Patent
Beckman et al.

(10) Patent No.: US 12,145,743 B2
(45) Date of Patent: Nov. 19, 2024

(54) ADAPTABLE LIGHTING SYSTEMS AND METHODS FOR AN INTERNAL CABIN OF A VEHICLE

(71) Applicant: THE BOEING COMPANY, Arlington, VA (US)

(72) Inventors: John Christiaan Beckman, Everett, WA (US); Julian K. Chang, Bothell, WA (US)

(73) Assignee: The Boeinng Company, Arlington, VA (US)

( * ) Notice: Subject to any disclaimer, the term of this patent is extended or adjusted under 35 U.S.C. 154(b) by 0 days.

(21) Appl. No.: 18/332,037

(22) Filed: Jun. 9, 2023

(65) Prior Publication Data
US 2024/0124154 A1 Apr. 18, 2024

Related U.S. Application Data

(60) Provisional application No. 63/416,010, filed on Oct. 14, 2022.

(51) Int. Cl.
*B64D 47/02* (2006.01)
*B64D 11/00* (2006.01)

(52) U.S. Cl.
CPC .............. *B64D 47/02* (2013.01); *B64D 11/00* (2013.01); *B64D 2011/0038* (2013.01); *B64D 2203/00* (2013.01)

(58) Field of Classification Search
None
See application file for complete search history.

(56) References Cited

U.S. PATENT DOCUMENTS

| 2012/0261981 A1 | 10/2012 | Carsten |
| 2014/0352625 A1 | 12/2014 | Reginhard |
| 2017/0286037 A1* | 10/2017 | Sizelove ............. H04W 12/088 |
| 2018/0081615 A1* | 3/2018 | Riedel ................ B64D 11/0015 |

(Continued)

FOREIGN PATENT DOCUMENTS

| DE | 102020210474 | 9/2021 |
| EP | 0943492 | 9/1999 |

(Continued)

OTHER PUBLICATIONS

Extended European Search Report for EP App. No. 23189931.1-1004, dated Jan. 19, 2024.

*Primary Examiner* — Richard G Davis
(74) *Attorney, Agent, or Firm* — Joseph M. Butscher; The Small Patent Law Group LLC

(57) ABSTRACT

A system and a method include a lighting sub-system including one or more light fixtures configured to be disposed within a cargo area of an internal cabin of a vehicle. A control unit is in communication with the one or more light fixtures. The control unit is configured to control the one or more light fixtures. The control unit is configured to selectively adjust light emitted from the one or more light fixtures based on the cargo within the cargo area. The system and the method can also include one or more temperature control devices configured to one or both of adjust or maintain a temperature within the cargo area of the internal cabin of the vehicle. The control unit can be configured to control the one or more temperature control devices based on the cargo within the cargo area.

23 Claims, 10 Drawing Sheets

(56) References Cited

U.S. PATENT DOCUMENTS

2018/0359985 A1* 12/2018 Jung ...................... B64D 11/00
2020/0150696 A1* 5/2020 Womble ............. G06K 7/10366

FOREIGN PATENT DOCUMENTS

| EP | 3417700 | 12/2018 | |
|---|---|---|---|
| WO | WO 2023/204708 | 10/2023 | |
| WO | WO-2023204708 A1 * | 10/2023 | ............. B64D 11/00 |

* cited by examiner

| Live Cargo Type | Equine | Livestock |
|---|---|---|
| Equine | breeding mares | Pigs |
| Livestock | race horses | Cattle |
| Foul | wild horses | Sheep |
| Aquatic | | |
| Flora | | |
| Insects | | |
| Exotics | | |
| Photobiological | Departure Location | Time at Departure location |
| Temporal | Seattle | 12am |
| Spatial | Chicago | 1 am |
| Intensity | Denver | 2 am |
| Spectral | New York | 3 am |
| | Doha | ---- |
| | | 10 am |
| | | |
| Photobiological | Radiation Direction from: | |
| Temporal | Ceiling Fixtures | |
| Spatial | Sidewall Fixtures | |
| Intensity | Ceiling + Sidewall FIxtures | |
| Spectral | (auto) | |
| Photobiological | Spectral Intensity | |
| Temporal | 5 lx | |
| Spatial | 50 lx | |
| Intensity | 75 lx | |
| Spectral | 100 lx | |
| | 1000 lx | |
| Photobiological | DD Spectrum ^ | Ceiling Fixtures |
| Temporal | 460nm | |
| Spatial | 555nm | on |
| Intensity | 660nm | |
| Spectral | 4000k white | |
| | 2300k white | off |
| Temperature | Diurnal Day ^ | Diurnal Day * |
| Diurnal Day | 45 F | 65 F |
| Diurnal Night | 50 F | 60F |
| Custom | 55 F | 55 F |
| | 65 F | |
| | 70 F | |

FIG. 9

Menu Example for Breeding Mares in

| Foul | Aquatic | Flora | Insects |
|---|---|---|---|
| Geese | Turtles | Cut flowers | Bees |
| Ducks | Dolphins | Seedlings | Ladybugs |
| Quail | Fish | Trees | Grasshoppers |
| Parrots | | | |
| | | | |
| | | | |
| Date of Departure | Arrival Location | Duration of Flight | Time of arrival |
| 1/15/2022 | Auckland, NZ | 2 hrs | 10 am |
| | Sydney, AU | 4 hrs | Noon |
| | Los Angeles, CA | — | 2 pm |
| | Seattle, WA | 10 hrs | 7 pm |
| | Santiago, Chile | 20 hrs | |
| | | 22 hrs | |

| Sidewall Fixtures | Ceiling + Sidewall | DN Spectrum * | Ceiling Fixtures |
|---|---|---|---|
| on | | 460 nm | off |
| on | on | 555 nm | |
| | | 660 nm | on |
| | | 4000k white | |
| off | off | 2300k white | |

FIG. 9 Cont.

Transport - Early Winter

| Exotics | Chronotype | |
|---|---|---|
| Elephants | Diurnal | |
| Large cats | Nocturnal | |
| Giraffes | Crepuscular | |
| Reptiles | Cathemeral | |
| Amphibians | | |
| | | |
| | | |
| Date of arrival | Diurnal Day (DD) length ^ | DD start time ^ |
| 1/16/2022 | 8 hrs | 8 am |
| 1/17/2022 | 10 hrs | 10 am |
| | 12 hrs | 8 pm |
| | 14 hrs | |
| | 16 hrs | |
| | 18 hrs | |
| | Custom | |

| Sidewall Fixtures | Ceiling +Sidewall | |
|---|---|---|
| off | off | |
| | | |
| on | off | |

FIG. 9 Cont.

| Diurnal Night (DN) length * | DN start time * |
|---|---|
| 4 hrs | 8 am |
| 5 hrs | 10 am |
| 8 hrs | 8 pm |
| 14 hrs | |
| 18 hrs | |
| Custom | |

FIG. 9 Cont.

ADAPTABLE LIGHTING SYSTEMS AND METHODS FOR AN INTERNAL CABIN OF A VEHICLE

RELATED APPLICATIONS

This application relates to and claims priority benefits from U.S. Provisional Patent Application No. 63/416,010, entitled "Adaptable Lighting Systems and Methods for an Internal Cabin of a Vehicle," filed Oct. 14, 2022, which is hereby incorporated by reference in its entirety.

FIELD OF THE DISCLOSURE

Examples of the present disclosure generally relate to adaptable lighting systems and methods for an internal cabin of a vehicle, such as can be used in relation to transportation of live cargo (for example, livestock, pets, plants, insects, and the like).

BACKGROUND OF THE DISCLOSURE

Aircraft, ships, trains, semi-trucks, spacecraft, and the like are used to transport passengers and cargo between various locations. For example, numerous aircraft depart from and arrive at a typical airport every day.

Certain commercial aircraft include an internal cabin that includes a passenger area. One or more cargo holds are disposed underneath or otherwise outside of the passenger area. As another example, cargo aircraft can include an internal cabin without a passenger area. In such aircraft, a substantial portion of the internal cabin is dedicated to cargo with only a seat row or two dedicated to personnel traveling with live cargo.

Cargo aircraft are often used to transport valuable live cargo, such as livestock, exotic animals, bees, horticulture products, race horses, and/or the like. Typically, cargo areas are illuminated by incandescent lights. Animals are often loaded into a cargo hold. The incandescent lights are turned off after the animals are onboard and cargo doors are closed. That is, the incandescent lights are selectively operated between on and off states. However, living beings within a cargo area of an aircraft may be adversely affected by such lighting. For example, pets can be frightened or otherwise anxious in dark environments when the incandescent lights are off.

SUMMARY OF THE DISCLOSURE

A need exists for an improved system and method for illuminating a cargo area of a vehicle. Further, a need exists for a lighting sub-system and method for a vehicle that can be adapted to benefit various types of live cargo.

With these needs in mind, certain examples of the present disclosure provide a system including a lighting sub-system including one or more light fixtures configured to be disposed within a cargo area of an internal cabin of a vehicle. A control unit is in communication with the one or more light fixtures. The control unit is configured to control the one or more light fixtures. The control unit is configured to selectively adjust light emitted from the one or more light fixtures based on the cargo within the cargo area.

In at least one example, the cargo includes one or more live animals. Further, the control unit can be configured to selectively adjust the light based on one or more of a temperature of the one or more live animals, a type of the one or more live animals, a duration of a trip of the vehicle, a phase of the trip of the vehicle, an origin of the trip, or a destination of the trip.

The system can also include one or more temperature control devices configured to one or both of adjust or maintain a temperature within the cargo area of the internal cabin of the vehicle. The control unit is configured to control the one or more temperature control devices based on the cargo within the cargo area.

In at least one example, the control unit is configured to selectively adjust one or both of the light or a temperature within the cargo area based on a cortisol level of the cargo.

In at least one example, the system includes one or more sensors in communication with the control unit. The one or more sensors are configured to sense one or more aspects of the cargo within the cargo area. The control unit can be configured to adjust the light emitted from the one or more light fixtures based on the one or more aspects. The control unit can be configured to adjust one or more temperature control devices based on the one or more aspects.

The system can also include a user interface in communication with the control unit.

The one or more light fixtures can include light emitters. The light emitters can include light emitting diodes (LEDs), which can be configured to selectively emit one or more of visible light, infrared radiation, and ultraviolet radiation.

In at least one example, the one or more light fixtures include a plurality of light fixtures. Each of the plurality of light fixtures can be disposed in a different zone of the cargo area.

Certain examples of the present disclosure provide a vehicle including an internal cabin having a cargo area. A lighting sub-system including one or more light fixtures is disposed within the cargo area. A control unit is in communication with the one or more light fixtures. The control unit is configured to control the one or more light fixtures. The control unit is configured to selectively adjust light emitted from the one or more light fixtures based on the cargo within the cargo area.

The vehicle can also include one or more temperature control devices configured to one or both of adjust or maintain a temperature within the cargo area. The control unit can be configured to control the one or more temperature control devices based on the cargo within the cargo area.

Certain examples of the present disclosure provide a method including controlling, by a control unit, one or more light fixtures of a lighting sub-system within a cargo area of an internal cabin of a vehicle. Said controlling, by the control unit, the one or more light fixtures includes selectively adjusting light emitted from the one or more light fixtures based on the cargo within the cargo area.

The method can also include controlling, by the control unit, one or more temperature control devices configured to one or both of adjust or maintain a temperature within the cargo area of the internal cabin of the vehicle. Said controlling, by the control unit, the one or more temperature control devices includes controlling the one or more temperature control devices based on the cargo within the cargo area.

BRIEF DESCRIPTION OF THE DRAWINGS

FIG. 9 illustrates an exemplary menu for various predetermined settings that can be selected for a lighting sub-system, according to an example of the present disclosure.

DETAILED DESCRIPTION OF THE DISCLOSURE

Figure 1:
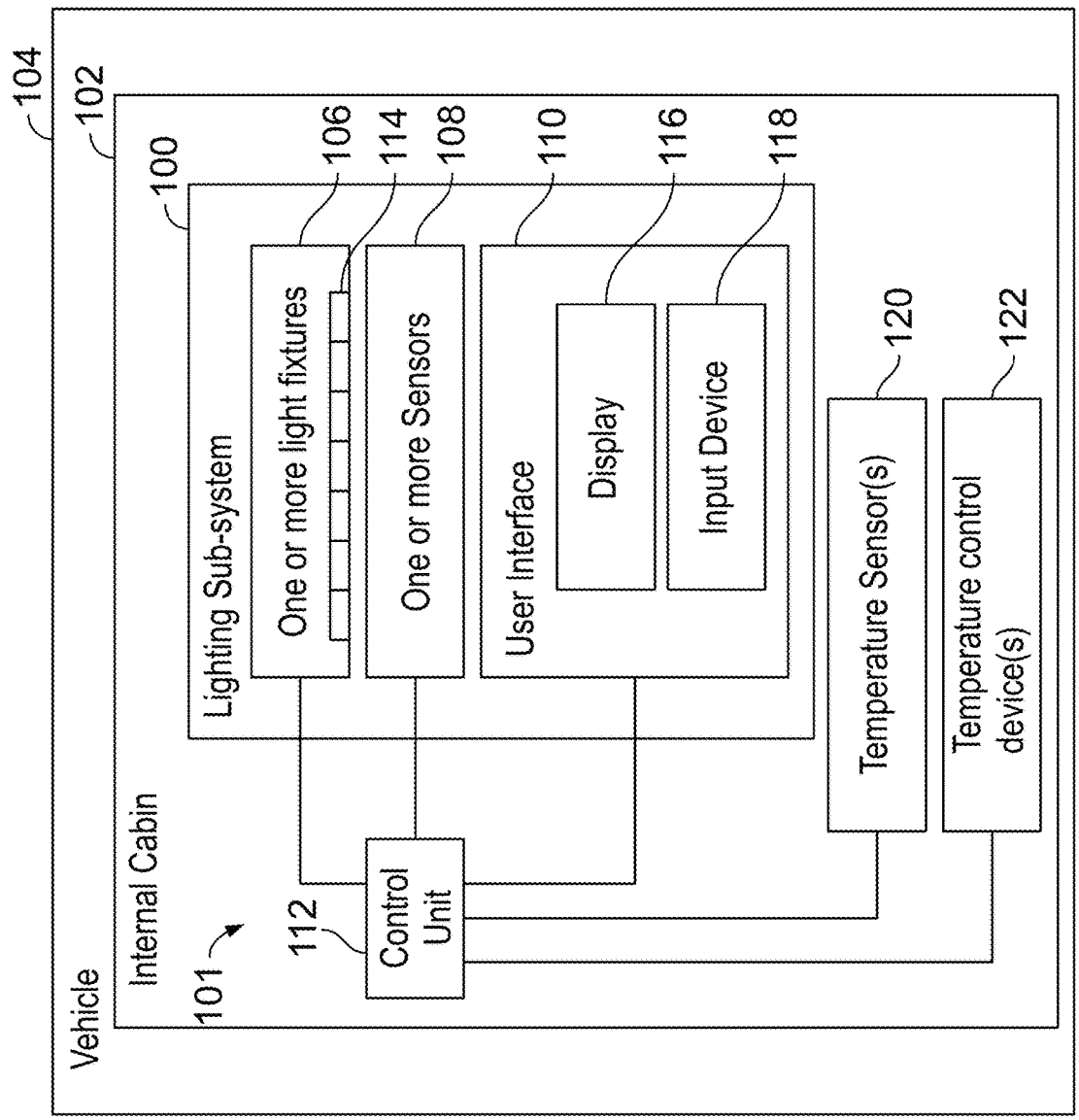
FIG. 1 illustrates a schematic block diagram for a lighting sub-system within an internal cabin of a vehicle, according to an example of the present disclosure.

The foregoing summary, as well as the following detailed description of certain examples will be better understood when read in conjunction with the appended drawings. As used herein, an element or step recited in the singular and preceded by the word "a" or "an" should be understood as not necessarily excluding the plural of the elements or steps. Further, references to "one example" are not intended to be interpreted as excluding the existence of additional examples that also incorporate the recited features. Moreover, unless explicitly stated to the contrary, examples "comprising" or "having" an element or a plurality of elements having a particular condition can include additional elements not having that condition.

Examples of the present disclosure provide systems and methods, such as can be used with vehicles. The systems and methods can be beneficially used to illuminate cargo areas of vehicles that hold live cargo, such as pets, plants, livestock, and various other forms of biological cargo.

Lighting science, physiological, and photobiological principles can be applied to provide animal welfare on cargo and freighter flights, for example. In at least one example, lighting sub-systems include solid state light fixtures that can be tunable, thereby providing a customizable lighting environment to various zones of a cargo area of a vehicle. Each species of animal, insect, or plant has unique needs in relation to photobiological and physiological welfare. The lighting sub-systems and methods described herein can be used to tailor an environment to the need of each carrier, each species, each type of cargo, and the like.

In at least one example, the lighting sub-systems and methods include one or more light emitting diodes (LEDs). In at least one example, the lighting sub-systems and methods utilize pulse width modulated (PWM) tunable LEDs, such as may include Red-Green-Blue (RGB) on printed circuit boards, which are controlled by a control unit and linked into the system architecture of a vehicle. Such systems and methods allow for customizable illumination and radiation variations within an internal cabin of a vehicle.

With solid state lighting sub-systems, such as RGB LEDs, illumination can be specifically tuned for a particular type of live cargo. For example, the systems and methods can vary a color temperature for the cargo depending on a particular need. Intensity of emitted light can be adjusted depending on the need. A light/dark photoperiod cycle can be varied depending on a circadian cycle of particular live cargo. As an example, one part of the cargo hold may have plants needing a mixture of blue light (seedlings) and UV for disease control, while another part of the cargo hold may carry breeder geese that benefit from red light (660 nm) at 30 lx during the transport period.

The systems and methods described herein allow for illumination tunability and control by operators to establish settings that are beneficial for particular types of cargo. The illumination can be adjusted for different areas, such as zones, grids, or the like within a cargo area. Control panels can be used to selectively activate and deactivate a lighting sub-system, as well as to control and adjust emitted light wavelength, intensity, duration, and the like. The lighting sub-system can be coupled to an environmental control system to deliver temperature and humidity unique requirements for each specific cargo zone or area for live cargo. The system can include a control panel including a control unit coupled to one or more light fixtures. Communication between the control unit and components of the lighting sub-system can be wired or wireless, such as via Bluetooth, Wi-Fi, infrared communication, and/or the like. The control panel can include touchscreen menus with selectable options based on current cargo. In at least one example, infrared thermography (IRT) scanners can be integrated into light fixtures, and can be used to evaluate livestock, such as with respect to potential disease, temperature of tissue, and/or the like. In at least one example, emitters and sensors for temperature of the cargo hold can be used to track motion of cargo animals for example. In at least one example, if a cargo zone exhibits less motion for a certain species, the illumination can auto tune to dimmer settings and warmer colors to prepare for sleep and melatonin onset, depending on needs of the species. If a crewmember needs to move to the cargo hold, infrared rays can trigger lighting needs for walkways instead of needing to rely on on/off toggle switches at control panels.

FIG. 1 illustrates a schematic block diagram for a lighting sub-system 100 within an internal cabin 102 of a vehicle 104, according to an example of the present disclosure. The internal cabin 102 can include a cargo area, such as a cargo hold underneath or otherwise separated from a passenger area. As another example, the internal cabin 102 may not include a passenger area, but may be dedicated to cargo. The vehicle 104 can be an aircraft, such as a commercial airliner. As another example, the vehicle 104 can be a land-based vehicle, such as a van, bus, trailer, train car, or the like. As another example, the vehicle 104 can be a watercraft, such as a cargo ship. As another example, the vehicle 104 can be a spacecraft.

FIG. 1 shows a system 101 for controlling one or more properties of an internal cabin and/or a portion thereof (such as a cargo area). In at least one example, the propert(ies) include one or more of lighting and/or temperature. For example, the system 101 can be configured to control light output by the lighting sub-system 100, a temperature output by one or more temperature control devices 122, and/or the like.

The lighting sub-system 100 includes one or more light fixtures 106, one or more sensors 108 (such as can include emitters and detectors), and a user interface 110. The light fixture(s) 106 are in communication with a control unit 112, such as through one or more wired or wireless connections. The sensor(s) 108 are in communication with the control unit 112, such as through one or more wired or wireless connections. The user interface 110 is in communication with the control unit 112, such as through one or more wired or wireless connections.

In at least one example, the lighting sub-system 100 includes the control unit 112. As another example, the control unit 112 is separate and distinct from the lighting sub-system 100.

The light fixture(s) 106 include one or more light emitters 114, such as solid state light emitters. For example, the light emitters 114 are LEDs that can selectively emit visible light (such as R-O-Y-G-B-I-V light from R-G-B LEDs), infrared radiation, and/or ultraviolet radiation. The control unit 112 is configured to control the light emitters 114 to emit a desired illumination at a desired wavelength within the internal cabin 102, such as within a cargo area of the internal cabin 102.

In at least one example, the light emitters 114 include one or more infrared radiation emitters, which can also be used to provide imaging capability in the dark, for example. For example, the infrared radiation emitters can be used to provide infrared illumination for camera imaging, such as in dark settings.

In at least one example, the light emitters 114 include one or more ultraviolet radiation emitters, which can also be used to identify liquid spills, such as urine or other biological matter, in cargo areas. In this manner, the ultraviolet radiation emitters can be used during cleaning processes, to identify certain areas that are in need of disinfection, sterilization, and/or other such cleaning. Further, the ultraviolet radiation emitters can be used to neutralize pathogens (such as bacteria, germs, viruses, and the like).

In at least one example, the light fixtures 106 are within the cargo area of the internal cabin 102. The light fixtures 106 can extend along a length of the cargo area. For example, the light fixtures 106 can extend along one or more of a ceiling, sidewalls, and a floor of the cargo area. The cargo area can include numerous zones that hold various types of live cargo. The control unit 112 is used to operate and control the light fixtures 106 in relation to each zone, depending on the type of live cargo within a particular zone.

In at least one example, the control unit 112 is also in communication with one or more temperature sensors 120, such as through one or more wired or wireless connections. The temperature sensors 120 can be separate and distinct from the sensor(s) 108. Optionally, the sensor(s) 108 can include one or more temperature sensors. The temperature sensor(s) 120 can be or otherwise include a thermometer, a thermostat, and/or the like. The temperature sensor(s) 120 are configured to detect a temperature within the internal cabin 102, and/or areas within the internal cabin 102.

In at least one example, the control unit 112 is also in communication with one or more temperature control devices 122, such as through one or more wired or wireless connections. The temperature control device(s) 122 can be or otherwise include a heater, an air conditioning unit, one or more fans, an environmental control system, and/or the like. The temperature control device(s) 122 are configured to selectively adapt and/or maintain a temperature within the internal cabin, and/or areas within the internal cabin 102.

In at least one example, the temperature sensor(s) 120 and the temperature control device(s) 122 include at least portions that are within the cargo area of the internal cabin 102. The control unit 112 can be used to operate and control the temperature control device(s) 122 based on temperatures detected by the temperature(s) 120 in relation to each zone, depending on the type of live cargo within a particular zone. Optionally, the control unit 112 may not be in communication with the temperature sensor(s) 120 and/or the temperature control device(s) 122. In at least one example, the control unit 112 is not configured to operate and control the temperature control device(s) 122.

The sensor(s) 108 are configured to detect one or more of temperature, light, motion, biomarkers including stress, cortisol levels, and/or the like. In at least one example, the sensor(s) 108 are or otherwise include optical sensors, such as infrared sensors. In at least one other example, the sensor(s) 108 can be ultrasonic sensors. As another example, the sensor(s) 108 can include thermometers. The control unit 112 receives signals from the sensor(s) 108 and can adjust illumination of the light fixture(s) 106 based on the received signals. Optionally, the control unit 122 receives temperature signals from the sensor(s) 108 (and/or the temperature sensor(s) 120), and can operate the temperature control device(s) 122 based on the temperature signals received to control temperature within one or more areas of the internal cabin 102, such as the cargo area and/or zones therein.

In at least one example, the sensor(s) 108 are within the cargo area of the internal cabin 102. The sensor(s) 108 can be part of the light fixture(s) 106, for example. Optionally, the sensor(s) 108 can be separate and distinct from the light fixture(s) 106. The light sensors 108 can extend along a length of the cargo area. For example, the sensors 108 can extend along one or more of a ceiling, sidewalls, and a floor of the cargo area. Alternatively, the lighting sub-system 100 does not include a sensor.

The user interface 110 includes a display 116 and an input device 118, both of which can be in communication with the control unit 112, such as through one or more wired or wireless connections. The display 116 can be a monitor, screen, television, touchscreen, and/or the like. The input device 118 can include a keyboard, mouse, stylus, touchscreen interface (that is, the input device 118 can be integral with the display 116), and/or the like.

In at least one example, the user interface 110 is a control panel secured to a portion of the internal cabin 102. For example, the user interface 110 can be mounted to a sidewall or monument within the internal cabin 102. As another example, the user interface 110 can be within a control area of the vehicle 104, such as a flight deck or cockpit. As another example, the user interface 110 can be part of a computer workstation within the internal cabin 102. As another example, the user interface 110 can be a handheld device, such as a smartphone, smart tablet, laptop computer, or the like.

In at least one example, the user interface 110 includes the control unit 112. In at least one other example, a light fixture 106 includes the control unit 112. As another example, the control unit 112 is separate and distinct from the light fixture(s) 106, the sensor(s) 108, and the user interface 110. For example, the control unit 112 can be part of a flight computer of an aircraft.

In at least one example, a user interface 110 can be in communication with and/or form a part of a flight computer of an aircraft. As another example, a user interface 110 can be part of a separate computer workstation aboard an aircraft. As another example, the user interface 110 can be a handheld device, such as a smart phone, tablet, or the like, within an aircraft. As another example, the user interface 110 can be located remotely from the aircraft, such as at an air traffic control location, a ground control location, a central monitoring center, and/or the like. A plurality of user interfaces 110 can be present such as within the vehicle 104, at a central monitoring center, and/or the like.

The control unit 112 can be in communication with the user interface(s) 110 through one or more wired (if at the same location), or wireless connections. For example, the control unit 112 can include a communication device, such as one or more antennas, transceivers, and/or the like, which allow for wireless communication with the user interface(s) 110. As another example, the control unit 112 and the user interface(s) 110 can be in communication through an intermediate medium, such as through the Internet, a private communication network, and/or the like.

In operation, the control unit 112 is used to control the light fixture(s) 106 to emit light at a desired wavelength(s), intensity, and duration. The control unit 112 is configured to customize the light emitted by the light emitters 114, as desired. In at least one example, the lighting sub-system 100 is configured to provide a customizable lighting environment to various zones of a cargo area of the vehicle 104. The lighting sub-system 100 is configured to tailor an environment based on a particular type of live cargo within the cargo area.

In at least one example, the light emitters 114 are or otherwise include solid state light emitters, such as a plurality of tunable LEDs. As such, the control unit 112 can operate the light fixtures 106 so that the light emitters 114 emit light that is specifically tuned for a particular type of live cargo, such as an animal, an insect, or a plant. As an example, the control unit 112 can vary a type, color temperature, spectral composition, intensity, illumination cycle, and/or the like of light emitted from the light emitters 114 of the light fixture(s) 106. In at least one example, the control unit 112 adjusts emitted light for different areas, such as zones, grids, or the like within a cargo area.

In at least one example, the control unit 112 is used to control the temperature control device(s) 122 to provide a desired temperature within one or more areas of the internal cabin 102. For example, the control unit 112 is configured to provide a customizable temperature to various zones of a cargo area of the vehicle 104. The control unit 112 is configured to tailor a temperature based on a particular type of live cargo within the cargo area.

The control unit 112 can operate the temperature control device(s) 122 to provide a temperature that is specifically tuned for a particular type of live cargo, such as an animal, an insect, or a plant. As an example, the control unit 112 can vary the output from the temperature control device(s) 122 to adjust and/or maintain a particular temperature. In at least one example, the control unit 112 adjusts temperature for different areas, such as zones, grids, or the like within a cargo area.

As described herein, the control unit 112 can be configured to control both light and temperature. In at least one example, one or more of the light fixtures 106 includes an optical temperature sensor that emits a signal to live animals. The signal reflected back to the optical temperature sensor may be indicative of a temperature that is above a recommended regulation threshold for such animals. The threshold is stored in a memory in communication with the control unit 112. The control unit 112 detects the reflected signal and compares it to the threshold, and operates the temperature control device(s) 122 (such as an environmental control system) accordingly, such as to lower the temperature for the benefit of the live cargo.

In at least one example, the control unit 112 can also be configured to adjust lighting and/or temperature based on a cortisol level of live cargo. For example, the sensors 108 can include infrared thermography sensors that are configured to scan the eyes, ears, hindquarters, or the like of livestock. In this manner, the sensor 108 can measure temperature emissivity of the area of the animal being scanned. The control unit 112 can then compare the measured temperature emissivity to a stored normal emissive factor for the animals. An elevated temperature indicates elevated cortisol or stress hormone levels. An elevated cortisol level typically disrupts the water content of an animal, thereby leading to water retention, which can lower a quality of meat of the animal, which can adversely affect a taste and a shelf life of such meat. Accordingly, the control unit 112 can be configured to adjust lighting and/or temperature of an area in which the animal is based on measured cortisol levels of the animal. Optionally, the control unit 112 may not be configured to adjust lighting and/or temperature based on cortisol measurement of live cargo.

In at least one example, the one or more sensors 108 can also be configured to detect sensors on cargo pallets within the internal cabin, such as within a cargo area. The control unit 112 can be configured to detect signals output by the emitting sensors of the cargo pallets, and detect a location, size, shape, and/or the like of the cargo pallets from the received signals. The control unit 112 can then output such information to one or more user interfaces, whether within the vehicle or remote therefrom, anywhere along a supply chain. Optionally, the control unit 112 may not be configured to detect signals output by emitting sensors of cargo pallets.

In at least one example, the system 101 includes the lighting sub-system 100 including one or more light fixtures 106 configured to be disposed within a cargo area of the internal cabin 102 of the vehicle 104. The control unit 112 is in communication with the one or more light fixtures 106. The control unit 112 is configured to control the one or more light fixtures 106. The control unit 112 is configured to selectively adjust light emitted from the one or more light fixtures 106 based on the cargo within the cargo area. In at least one example, the system 101 can also include one or more temperature control devices 122 configured to adjust and/or maintain a temperature within the cargo area of the internal cabin 102 of the vehicle 104. The control unit 112 can be further configured to control the one or more temperature control devices 122 based on the cargo within the cargo area.

In at least one example, the cargo includes one or more live animals (such as horses, dogs, cats, or the like). The control unit 112 can be configured to selectively adjust the light based on one or more of a temperature of the one or more live animals, a type of the one or more live animals, a duration of a trip (such as a flight) of the vehicle (such as a commercial aircraft), a phase (such as takeoff, climb, cruise, descent, or landing) of the trip of the vehicle, an origin (such as a departure airport) of the trip, or a destination (such as an arrival airport) of the trip.

As used herein, the term "control unit," "central processing unit," "CPU," "computer," or the like may include any processor-based or microprocessor-based system including systems using microcontrollers, reduced instruction set computers (RISC), application specific integrated circuits (ASICs), logic circuits, and any other circuit or processor including hardware, software, or a combination thereof capable of executing the functions described herein. Such are exemplary only, and are thus not intended to limit in any way the definition and/or meaning of such terms. For example, the control unit 112 may be or include one or more processors that are configured to control operation, as described herein.

The control unit 112 is configured to execute a set of instructions that are stored in one or more data storage units or elements (such as one or more memories), in order to process data. For example, the control unit 112 may include or be coupled to one or more memories. The data storage units may also store data or other information as desired or needed. The data storage units may be in the form of an information source or a physical memory element within a processing machine.

The set of instructions may include various commands that instruct the control unit 112 as a processing machine to perform specific operations such as the methods and processes of the various examples of the subject matter described herein. The set of instructions may be in the form of a software program. The software may be in various forms such as system software or application software. Further, the software may be in the form of a collection of separate programs, a program subset within a larger program, or a portion of a program. The software may also include modular programming in the form of object-oriented programming. The processing of input data by the processing machine may be in response to user commands, or in response to results of previous processing, or in response to a request made by another processing machine.

The diagrams of examples herein may illustrate one or more control or processing units, such as the control unit 112. It is to be understood that the processing or control units may represent circuits, circuitry, or portions thereof that may be implemented as hardware with associated instructions (e.g., software stored on a tangible and non-transitory computer readable storage medium, such as a computer hard drive, ROM, RAM, or the like) that perform the operations described herein. The hardware may include state machine circuitry hardwired to perform the functions described herein. Optionally, the hardware may include electronic circuits that include and/or are connected to one or more logic-based devices, such as microprocessors, processors, controllers, or the like. Optionally, the control unit 112 may represent processing circuitry such as one or more of a field programmable gate array (FPGA), application specific integrated circuit (ASIC), microprocessor(s), and/or the like. The circuits in various examples may be configured to execute one or more algorithms to perform functions described herein. The one or more algorithms may include aspects of examples disclosed herein, whether or not expressly identified in a flowchart or a method.

As used herein, the terms "software" and "firmware" are interchangeable, and include any computer program stored in a data storage unit (for example, one or more memories) for execution by a computer, including RAM memory, ROM memory, EPROM memory, EEPROM memory, and non-volatile RAM (NVRAM) memory. The above data storage unit types are exemplary only, and are thus not limiting as to the types of memory usable for storage of a computer program.

Figure 2:
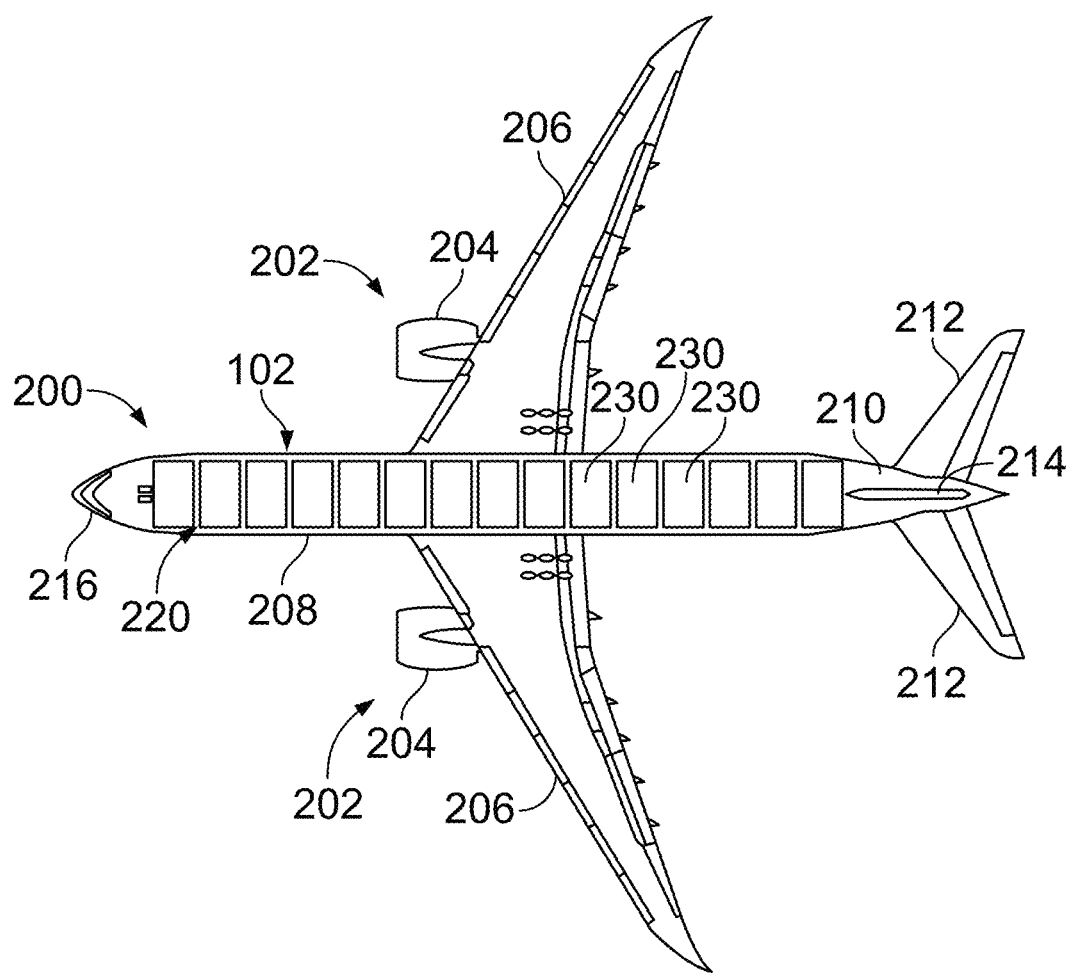
FIG. 2 illustrates a top plan view of an aircraft, according to an example of the present disclosure.

FIG. 2 illustrates a top plan view of an aircraft 200, according to an example of the present disclosure. The aircraft 200 is an example of the vehicle 104, shown in FIG. 1. The aircraft 200 includes a propulsion system 202 that includes engines 204, for example. Optionally, the propulsion system 202 may include more engines 204 than shown. The engines 204 are carried by wings 206 of the aircraft 200. In other examples, the engines 204 may be carried by a fuselage 208 and/or an empennage 210. The empennage 210 may also support horizontal stabilizers 212 and a vertical stabilizer 214. The fuselage 208 of the aircraft 200 defines an internal cabin 102, which includes a flight deck or cockpit 216. FIG. 2 shows an example of an aircraft 200. It is to be understood that the aircraft 200 can be sized, shaped, and configured differently than shown in FIG. 2.

The internal cabin 102 includes a cargo area 220. In at least one example, the cargo area 220 is underneath a passenger area of the internal cabin 102. As another example, the internal cabin 102 may not include a passenger area, and the cargo area 220 extends throughout substantially all of the internal cabin 102 (with the exception of the flight deck or cockpit 216). The cargo area 220 can include numerous zones 230 configured to hold different types of cargo, such as various types of live cargo. Referring to FIGS. 1 and 2, the lighting sub-system 100 can be used to illuminate the cargo area 220, including the zones 230, as desired. Further, the control unit 112 can be configured to control temperature within the zones 230, as desired.

Figure 3:
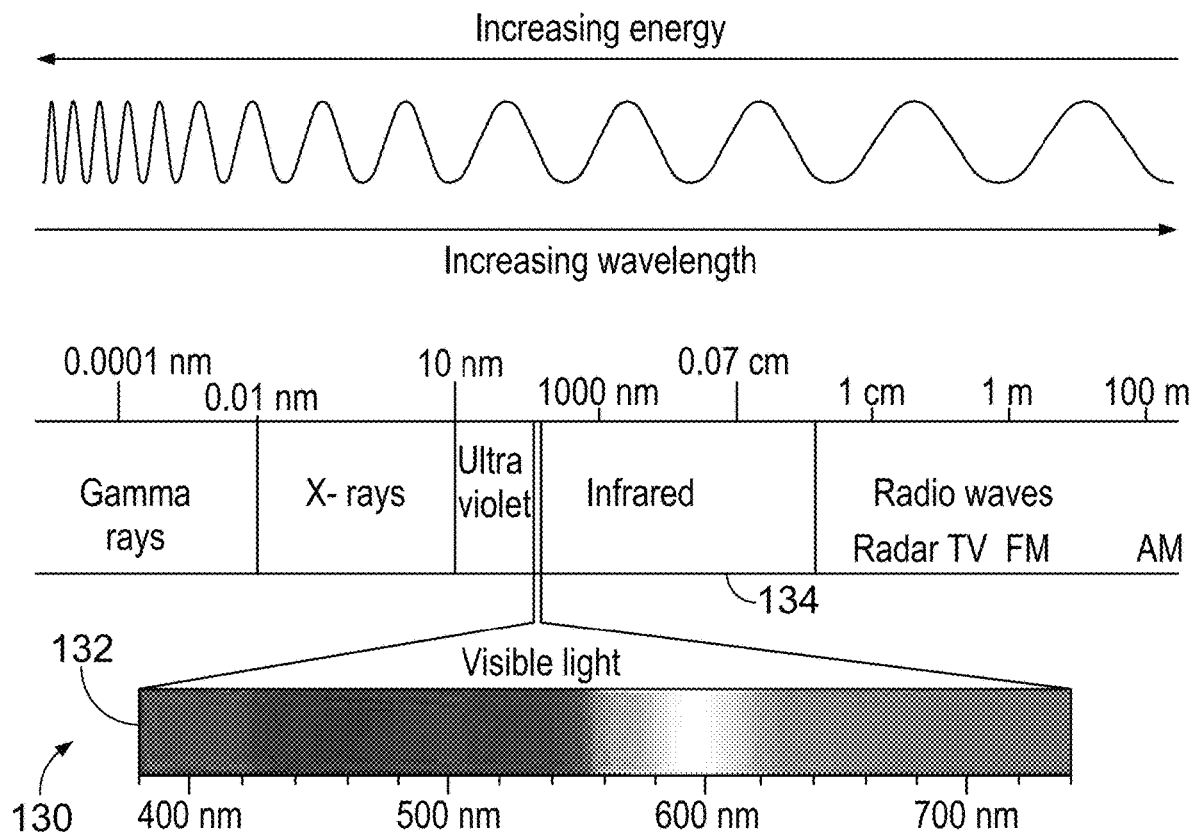
FIG. 3 illustrates the electromagnetic spectrum.

FIG. 3 illustrates the electromagnetic spectrum 130. The light spectrum 130 includes visible light wavelengths 132 and invisible light wavelengths 134, such as infrared wavelengths and/or ultraviolet wavelengths. Referring to FIGS. 1-3, the light emitters 114, such as LEDs, are configured to selectively and adaptively emit visible light, infrared radiation, and/or ultraviolet radiation, as desired, and as controlled by the control unit 112. The light emitters 114 can be multi-band light emitters configured to emit visible light and invisible light, for example.

Figure 4:
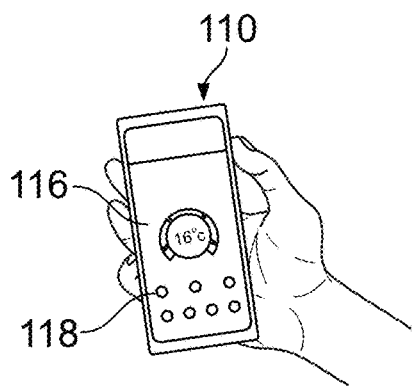
FIG. 4 illustrates a front view of a user interface, according to an example of the present disclosure.

FIG. 4 illustrates a front view of a user interface 110, according to an example of the present disclosure. In at least one example, the user interface 110 is a handheld device that integrates the display 116 and the input device 118 into a touchscreen interface.

Figure 5:
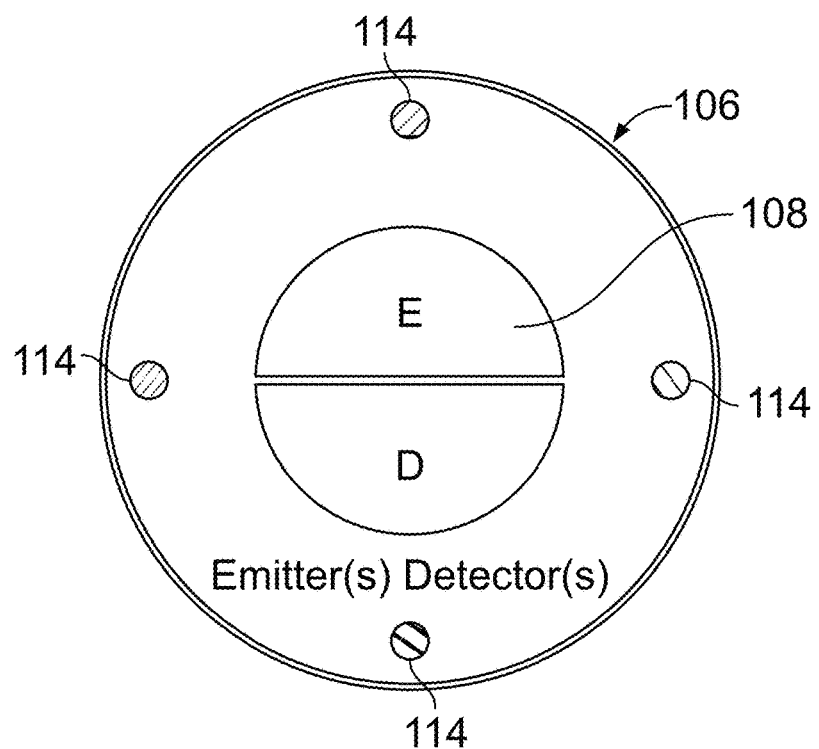
FIG. 5 illustrates a front view of a light fixture, according to an example of the present disclosure.

FIG. 5 illustrates a front view of a light fixture 106, according to an example of the present disclosure. As shown in FIG. 5, the light fixture 106 includes light emitters 114, and a sensor 108. The light emitters 114 can include a red light emitter, a green light emitter, and a blue light emitter. The light emitters 114 can also include an infrared radiation emitter. Optionally, the sensor 108 can be separate and distinct from the light fixture 106.

Figure 6:
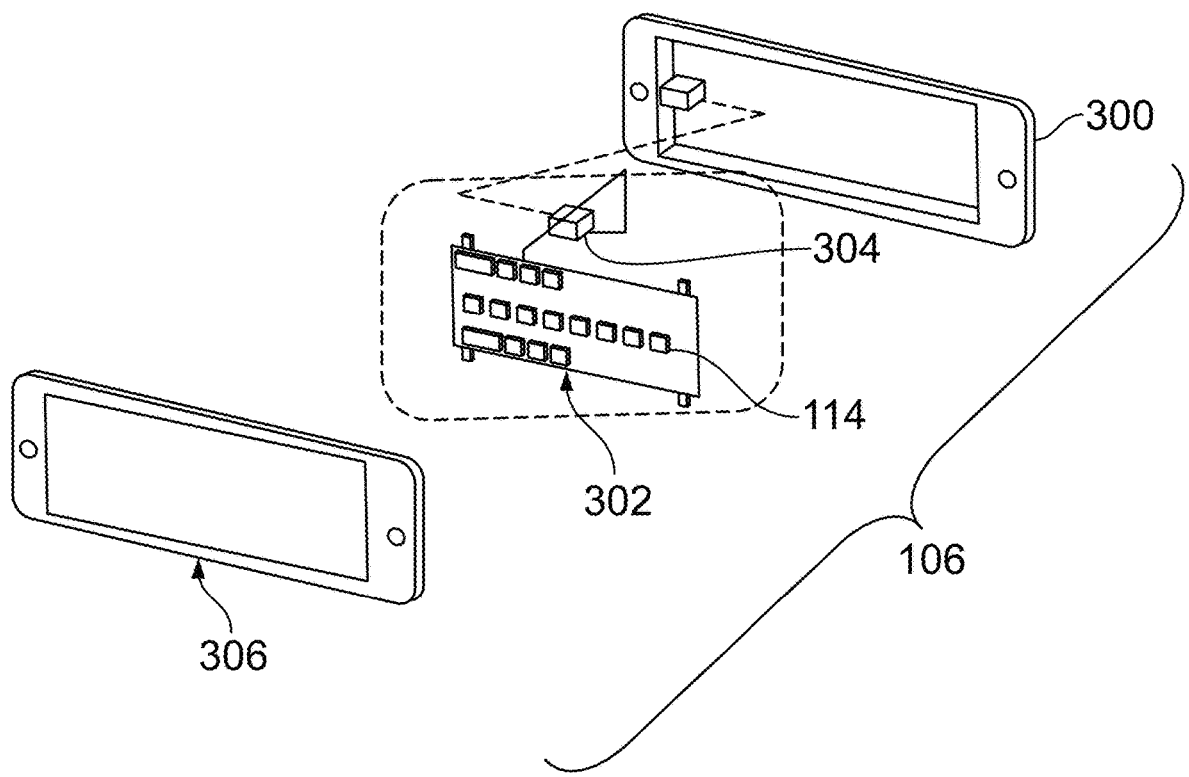
FIG. 6 illustrates an isometric exploded view of a light fixture, according to an example of the present disclosure.

FIG. 6 illustrates an isometric exploded view of a light fixture 106, according to an example of the present disclosure. In at least one example, the light fixture 106 includes a housing 300, which is configured to be mounted on and/or within a wall, a ceiling a floor, or the like. The housing 300 receives and retains a circuit board 302 on which light emitters 114 are secured. A communication device 304 can be secured to the housing 300 and/or the circuit board 302 and is in communication with the light emitters 114. The communication device 304 can be a wireless receiver, transmitter, transponder, or the like that is configured to communicate with the control unit 112 (shown in FIG. 1). For example, the communication device 304 can be a Bluetooth, WiFi, or infrared signal receiver. The light fixture 106 can also include a lens 306 that secures over the light emitters 114.

The light fixture 106 can be sized, shaped, and configured differently than shown in FIG. 6. The light fixture 106 can include more or less light emitters 114 than shown.

Figure 7:
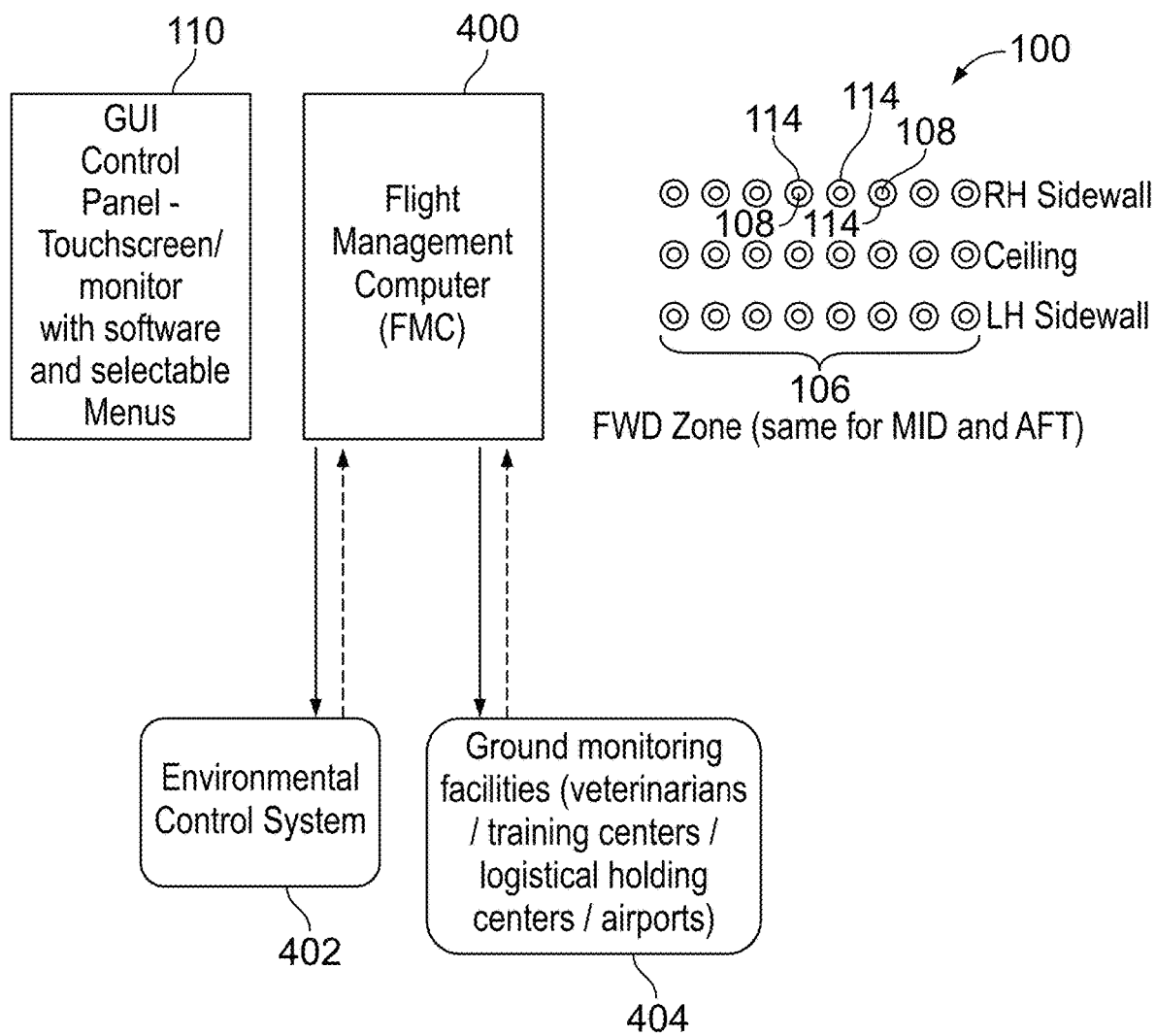
FIG. 7 illustrates a schematic block diagram of a lighting sub-system, according to an example of the present disclosure.

FIG. 7 illustrates a schematic block diagram of a lighting sub-system 100, according to an example of the present disclosure. The light fixtures 106 are in communication with a flight management computer 400, which can include the control unit 112 (shown in FIG. 1). The user interface 110 is in communication with the flight management computer 400 of an aircraft. The flight management computer 400 is also in communication with an environmental control system 402 and ground monitoring facilities 404, such as through one or more wired or wireless connections.

The light fixtures 106 include tunable light emitters that are controlled by the flight management computer 400. The sensors 108 can be or otherwise include infrared thermography sensors, passive motion infrared sensor, active infrared presence sensor, false color sensors, and/or the like.

Figure 8:
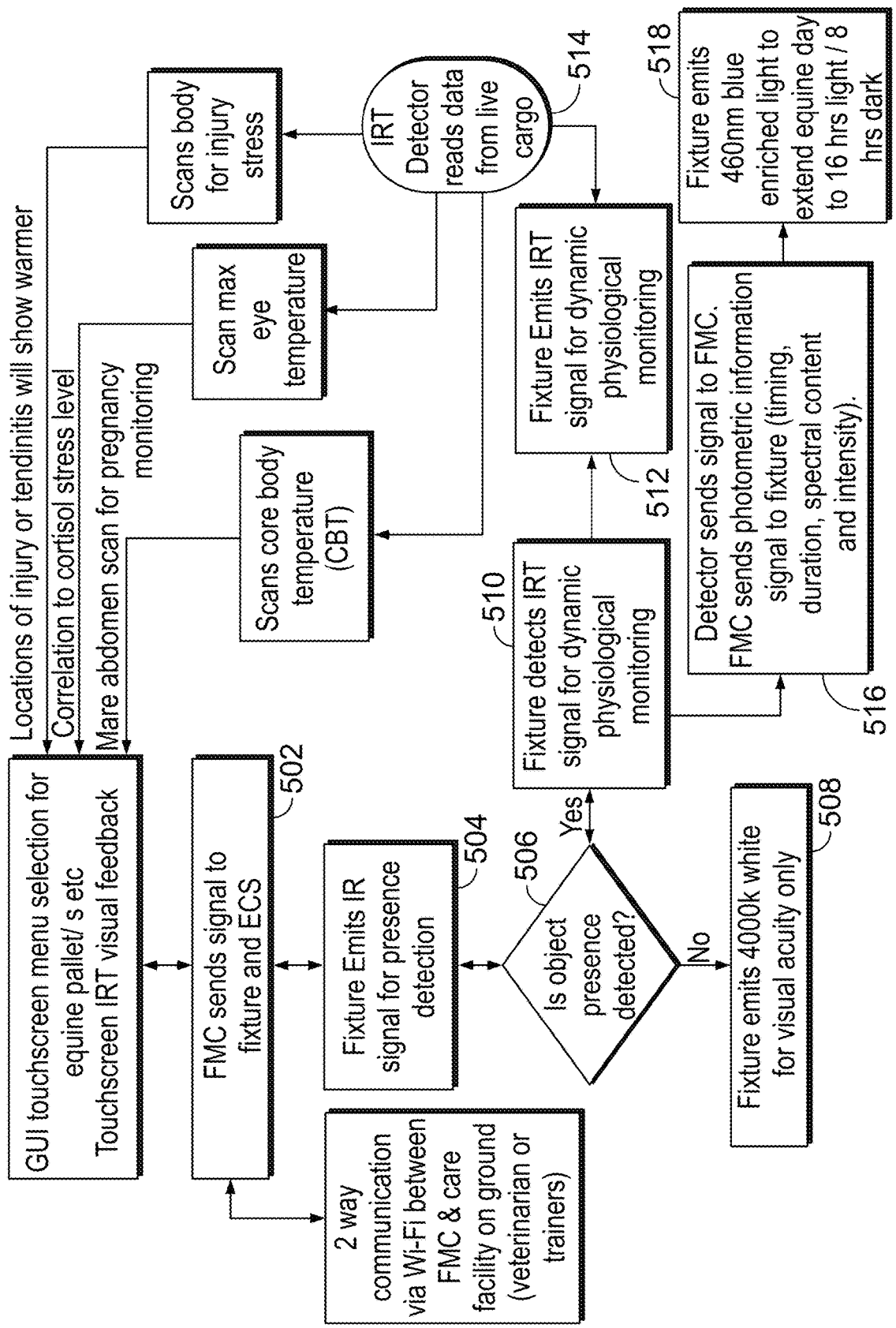
FIG. 8 illustrates a flow chart of operating a lighting sub-system, according to an example of the present disclosure.

FIG. 8 illustrates a flow chart of operating a lighting sub-system, according to an example of the present disclosure. FIG. 8 shows an example of operating a lighting sub-system within a cargo area that holds equine thoroughbred breeding mares. As shown, the sensors can sense various aspects of the live cargo, such as body temperature, eye temperature, physical stress, and the like. The lighting sub-system can automatically operate and change characteristics of emitted light based on the sensed aspects.

Referring to FIGS. 1 and 8, in at least one example, at 500, the user interface 110 is operated to select a type of live cargo. At 502, the control unit 112 sends a signal to the lighting sub-system 100 and/or the temperature control device(s) 122. In at least one example, there can be two way communication between the control unit 112 and a care provider for the live cargo (such as a veterinarian or a trainer).

At 504, one or more of the light fixtures 106 emits an infrared signal to detect presence of the live cargo. At 506, the control unit 112 determines if an object is detected (such as via the sensor(s) 108 receiving a reflected signal). If not, the method proceeds to 508, at which the control unit 112 operates the one or more light fixtures 106 to emit 4000K white light for visual acuity only.

If, however, an object is detected at 506, the method proceeds to 510, at which the sensor(s) 108 detect reflection of signals having a predefined wavelength (such as associated with a particular type of live cargo), and then at 512, the control unit 122 controls the lighting sub-system to emit an infrared signal for dynamic physiological monitoring. The method then proceeds to 514, at which control unit 112 receives data from the sensor(s) 108.

In response to detecting the reflected signals at 510, the control unit 112 also outputs one or more photometric information signals to the lighting sub-system 100. Such information includes timing, duration, spectral content, intensity, and/or the like, which controls operation of the light fixture(s) 106. At 518, the light fixture(s) 106 are controlled accordingly, such as by emitting blue enriched light to provide lighting for equine based on 16 hours of light and 8 hours of dark. As shown, the sensors 108 can be used to scan core body temperature, eye temperature, and injury stress of the live cargo.

FIG. 9 illustrates an exemplary menu for various predetermined settings that can be selected for a lighting sub-system, according to an example of the present disclosure. As shown, the menu can include various selections for types of livestock, departure and arrival information, and various physiological information. Referring to FIGS. 1 and 9, such information can be stored in a memory of the control unit 112, which can operate the lighting sub-system 100 and/or the temperature control device(s) 122 based on signals received from the sensor(s) 108 (and/or the temperature sensor(s) 120).

Further, the disclosure comprises examples according to the following clauses:

Clause 1. A system comprising:
a lighting sub-system including one or more light fixtures configured to be disposed within a cargo area of an internal cabin of a vehicle; and
a control unit in communication with the one or more light fixtures, the control unit configured to control the one or more light fixtures, and
wherein the control unit is configured to selectively adjust light emitted from the one or more light fixtures based on cargo within the cargo area.

Clause 2. The system of Clause 1, further comprising one or more temperature control devices configured to one or both of adjust or maintain a temperature within the cargo area of the internal cabin of the vehicle, wherein the control unit is configured to control the one or more temperature control devices based on the cargo within the cargo area.

Clause 3. The system of Clauses 1 or 2, wherein the control unit is configured to selectively adjust one or both of the light or a temperature within the cargo area based on a cortisol level of the cargo.

Clause 4. The system of any of Clauses 1-3, further comprising one or more sensors in communication with the control unit, the one or more sensors configured to sense one or more aspects of the cargo within the cargo area.

Clause 5. The system of Clause 4, wherein the control unit is configured to adjust the light emitted from the one or more light fixtures based on the one or more aspects.

Clause 6. The system of Clauses 4 or 5, wherein the control unit is configured to adjust one or more temperature control devices based on the one or more aspects.

Clause 7. The system of any of Clauses 1-6, further comprising a user interface in communication with the control unit.

Clause 8. The system of any of Clauses 1-7, wherein the one or more light fixtures comprise light emitters.

Clause 9. The system of Clause 8, wherein the light emitters comprise light emitting diodes (LEDs).

Clause 10. The system of Clause 9, wherein the LEDs are configured to selectively emit one or more of visible light, infrared radiation, and ultraviolet radiation.

Clause 11. The system of any of Clauses 1-10, wherein the one or more light fixtures comprise a plurality of light fixtures, and wherein each of the plurality of light fixtures is disposed in a different zone of the cargo area.

Clause 12. A vehicle comprising:
an internal cabin having a cargo area;
a lighting sub-system including one or more light fixtures disposed within the cargo area; and
a control unit in communication with the one or more light fixtures, the control unit configured to control the one or more light fixtures, and
wherein the control unit is configured to selectively adjust light emitted from the one or more light fixtures based on cargo within the cargo area.

Clause 13. The vehicle of Clause 12, further comprising one or more temperature control devices configured to one or both of adjust or maintain a temperature within the cargo area, wherein the control unit is configured to control the one or more temperature control devices based on the cargo within the cargo area.

Clause 14. The vehicle of Clauses 12 or 13, further comprising one or more sensors in communication with the control unit, the one or more sensors configured to sense one or more aspects of the cargo within the cargo area.

Clause 15. The vehicle of Clause 14, wherein the control unit is configured to adjust the light emitted from the one or more light fixtures and the one or more temperature control devices based on the one or more aspects.

Clause 16. The vehicle of any of Clauses 12-15, further comprising a user interface in communication with the control unit.

Clause 17. The vehicle of any of Clauses 12-16, wherein the one or more light fixtures comprise light emitters, and wherein the light emitters comprise light emitting diodes (LEDs) configured to selectively emit one or more of visible light, infrared radiation, and ultraviolet radiation.

Clause 18. The vehicle of any of Clauses 12-17, wherein the one or more light fixtures comprise a plurality of light fixtures, and wherein each of the plurality of light fixtures is disposed in a different zone of the cargo area.

Clause 19. A method comprising:
controlling, by a control unit, one or more light fixtures of a lighting sub-system within a cargo area of an internal cabin of a vehicle, wherein said controlling, by the control unit, the one or more light fixtures comprises selectively adjusting light emitted from the one or more light fixtures based on the cargo within the cargo area.

Clause 20. The method of Clause 19, further comprising controlling, by the control unit, one or more temperature control devices configured to one or both of adjust or maintain a temperature within the cargo area of the internal cabin of the vehicle, wherein said controlling, by the control unit, the one or more temperature control devices comprises controlling the one or more temperature control devices based on cargo within the cargo area.

Clause 21. The system or method of any of claims 1-20, wherein the cargo includes one or more live animals, and wherein the control unit is configured to selectively adjust the light based on one or more of a temperature of the one or more live animals, a type of the one or more live animals, a duration of a trip of the vehicle, a phase of the trip of the vehicle, an origin of the trip, or a destination of the trip.

As described herein, examples of the present disclosure provide improved systems and methods for illuminating a cargo area of a vehicle. Further, examples of the present disclosure provide lighting sub-systems and methods for a vehicle that can be adapted to benefit various types of live cargo.

While various spatial and directional terms, such as top, bottom, lower, mid, lateral, horizontal, vertical, front and the like can be used to describe examples of the present disclosure, it is understood that such terms are merely used with respect to the orientations shown in the drawings. The orientations can be inverted, rotated, or otherwise changed, such that an upper portion is a lower portion, and vice versa, horizontal becomes vertical, and the like.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

It is to be understood that the above description is intended to be illustrative, and not restrictive. For example, the above-described examples (and/or aspects thereof) can be used in combination with each other. In addition, many modifications can be made to adapt a particular situation or material to the teachings of the various examples of the disclosure without departing from their scope. While the dimensions and types of materials described herein are intended to define the aspects of the various examples of the disclosure, the examples are by no means limiting and are exemplary examples. Many other examples will be apparent to those of skill in the art upon reviewing the above description. The scope of the various examples of the disclosure should, therefore, be determined with reference to the appended claims, along with the full scope of equivalents to which such claims are entitled. In the appended claims and the detailed description herein, the terms "including" and "in which" are used as the plain-English equivalents of the respective terms "comprising" and "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various examples of the disclosure, including the best mode, and also to enable any person skilled in the art to practice the various examples of the disclosure, including making and using any devices or systems and performing any incorporated methods. The patentable scope of the various examples of the disclosure is defined by the claims, and can include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A system comprising:
a lighting sub-system including one or more light fixtures configured to be disposed within a cargo area of an internal cabin of a vehicle;
a control unit in communication with the one or more light fixtures, the control unit configured to control the one or more light fixtures; and
one or more temperature control devices configured to one or both of adjust or maintain a temperature within the cargo area of the internal cabin of the vehicle,
wherein the control unit is configured to:
selectively adjust light emitted from the one or more light fixtures based on cargo within the cargo area, and
control the one or more temperature control devices based on the cargo within the cargo area.

2. The system of claim 1, wherein the cargo includes one or more live animals, and wherein the control unit is configured to selectively adjust the light based on one or more of a temperature of the one or more live animals, a type of the one or more live animals, a duration of a trip of the vehicle, a phase of the trip of the vehicle, an origin of the trip, or a destination of the trip.

3. The system of claim 1, wherein the control unit is further configured to selectively adjust one or both of the light or a temperature within the cargo area based on a cortisol level of the cargo.

4. The system of claim 1, further comprising one or more sensors in communication with the control unit, the one or more sensors configured to sense one or more aspects of the cargo within the cargo area.

5. The system of claim 4, wherein the control unit is configured to adjust the light emitted from the one or more light fixtures based on the one or more aspects.

6. The system of claim 4, wherein the control unit is configured to adjust one the or more temperature control devices based on the one or more aspects.

7. The system of claim 1, further comprising a user interface in communication with the control unit.

8. The system of claim 1, wherein the one or more light fixtures comprise light emitters.

9. The system of claim 8, wherein the light emitters comprise light emitting diodes (LEDs).

10. The system of claim 9, wherein the LEDs are configured to selectively emit one or more of visible light, infrared radiation, and ultraviolet radiation.

11. The system of claim 1, wherein the one or more light fixtures comprise a plurality of light fixtures, and wherein each of the plurality of light fixtures is disposed in a different zone of the cargo area.

12. A vehicle comprising:
an internal cabin having a cargo area;
a lighting sub-system including one or more light fixtures disposed within the cargo area;
a control unit in communication with the one or more light fixtures, the control unit configured to control the one or more light fixtures; and
one or more temperature control devices configured to one or both of adjust or maintain a temperature within the cargo area,
wherein the control unit is configured to;
selectively adjust light emitted from the one or more light fixtures based on the cargo within the cargo area, and
control the one or more temperature control devices based on the cargo within the cargo area.

13. The vehicle of claim 12, wherein the cargo includes one or more live animals, and wherein the control unit is configured to selectively adjust the light based on one or more of a temperature of the one or more live animals, a type of the one or more live animals, a duration of a trip of the vehicle, a phase of the trip of the vehicle, an origin of the trip, or a destination of the trip.

14. The vehicle of claim 12, further comprising one or more sensors in communication with the control unit, the one or more sensors configured to sense one or more aspects of the cargo within the cargo area.

15. The vehicle of claim 14, wherein the control unit is further configured to adjust the light emitted from the one or more light fixtures and the one or more temperature control devices based on the one or more aspects.

16. The vehicle of claim 12, further comprising a user interface in communication with the control unit.

17. The vehicle of claim 12, wherein the one or more light fixtures comprise light emitters, and wherein the light emitters comprise light emitting diodes (LEDs) configured to selectively emit one or more of visible light, infrared radiation, and ultraviolet radiation.

18. The vehicle of claim 12, wherein the one or more light fixtures comprise a plurality of light fixtures, and wherein each of the plurality of light fixtures is disposed in a different zone of the cargo area.

19. A method comprising:
controlling, by a control unit, one or more light fixtures of a lighting sub-system within a cargo area of an internal cabin of a vehicle, wherein said controlling, by the control unit, the one or more light fixtures comprises selectively adjusting light emitted from the one or more light fixtures based on cargo within the cargo area; and
controlling, by the control unit, one or more temperature control devices configured to one or both of adjust or maintain a temperature within the cargo area of the internal cabin of the vehicle, wherein said controlling, by the control unit, the one or more temperature control devices comprises controlling the one or more temperature control devices based on the cargo within the cargo area.

20. The method of claim 19, wherein the cargo includes one or more live animals, and wherein said selectively adjusting comprises selectively adjusting the light based on one or more of a temperature of the one or more live animals, a type of the one or more live animals, a duration of a trip of the vehicle, a phase of the trip of the vehicle, an origin of the trip, or a destination of the trip.

21. A system comprising:
a lighting sub-system including one or more light fixtures configured to be disposed within a cargo area of an internal cabin of a vehicle; and
a control unit in communication with the one or more light fixtures,
wherein the control unit is configured to selectively adjust one or both of light emitted from the one or more light fixtures, or a temperature within the cargo area based on a cortisol level of cargo within the cargo area.

22. A system comprising:
a lighting sub-system including one or more light fixtures configured to be disposed within a cargo area of an internal cabin of a vehicle;
a control unit in communication with the one or more light fixtures, the control unit configured to control the one or more light fixtures; and
one or more sensors in communication with the control unit, the one or more sensors configured to sense one or more aspects of the cargo within the cargo area,
wherein the control unit is configured to:
selectively adjust light emitted from the one or more light fixtures based on cargo within the cargo area, and
adjust one or more temperature control devices based on the one or more aspects.

23. A vehicle comprising:
an internal cabin having a cargo area;
a lighting sub-system including one or more light fixtures disposed within the cargo area;
a control unit in communication with the one or more light fixtures, the control unit configured to control the one or more light fixtures; and
one or more sensors in communication with the control unit, the one or more sensors configured to sense one or more aspects of the cargo within the cargo area,
wherein the control unit is configured to:
selectively adjust light emitted from the one or more light fixtures based on the one or more aspects of the cargo within the cargo area, and
adjust one or more temperature control devices based on the one or more aspects of the cargo within the cargo area.

* * * * *